(12) United States Patent
Dadson (10) Patent No.: US 6,228,047 B1
(45) Date of Patent: May 8, 2001

(54) METHOD AND APPARATUS FOR PERFORMING PERITONEAL DIALYSIS

(75) Inventor: Joseph E. Dadson, Richmond Hill (CA)

(73) Assignee: 1274515 Ontario Inc., Scarborough (CA)

(*) Notice: Subject to any disclaimer, the term of this patent is extended or adjusted under 35 U.S.C. 154(b) by 0 days.

(21) Appl. No.: 09/468,586

(22) Filed: Dec. 21, 1999

Related U.S. Application Data (63) Continuation-in-part of application No. 09/122,692, filed on Jul. 27, 1998, now abandoned.

(30) Foreign Application Priority Data

Jul. 28, 1997  (CA) .................................................... 2211848

(51) Int. Cl.$^7$ .............................. A61M 1/00; A61B 19/00
(52) U.S. Cl. .............................................. 604/29; 604/407
(58) Field of Search ............................ 604/27, 29–34, 604/89, 91, 131, 407; 137/625, 625.11, 627.5, 625.67

(56) References Cited

U.S. PATENT DOCUMENTS

| | | | |
|---|---|---|---|
| 4,620,846 | * 11/1986 | Goldberg et al. | 604/28 |
| 4,915,688 | * 4/1990 | Bischof et al. | 604/83 |
| 5,004,459 | * 4/1991 | Peabody et al. | 604/29 |
| 5,083,872 | * 1/1972 | Farling et al. | 366/138 |
| 5,152,743 | * 10/1992 | Gorsuch et al. | 604/4 |
| 5,344,392 | * 9/1994 | Senninger et al. | 604/4 |
| 5,643,201 | * 7/1997 | Peabody et al. | 604/31 |
| 5,800,397 | * 9/1998 | Wilson et al. | 604/151 |

* cited by examiner

*Primary Examiner*—Richard K. Seidel
*Assistant Examiner*—Michael J. Hayes
(74) *Attorney, Agent, or Firm*—Ridout & Maybee (57) ABSTRACT

An automated peritoneal dialysis machine is provided which is capable of selecting and changing the composition of dialysate delivered to a patient in the course of treatment to meet specific physiological needs. The apparatus includes means for metering solutions of osmotic agent, electrolytes and other desired dialysate components from separate solution containers into mixing chamber means for combination in desired proportions. The means for delivery of fresh dialysis fluid to a patient and for removing spent dialysis fluid from the patient includes means for monitoring intraperitoneal pressure and other conditions of the fluid in the peritoneum and electronic control means responsible to the signal of monitoring means for controlling rates of dialysate infusion and removal.

19 Claims, 7 Drawing Sheets

METHOD AND APPARATUS FOR PERFORMING PERITONEAL DIALYSIS

This invention relates to a new machine and method for carrying out automated peritoneal dialysis (PD).

RELATED APPLICATION

This application is a continuation-in-part of U.S. patent application Ser. No. 09/122,692 filed Jul. 27, 1998, now abandoned, and entitled "METHOD AND APPARATUS FOR PERFORMING PERITONEAL DIALYSIS".

BACKGROUND OF THE INVENTION

Unlike the extra corporeal system used in hemodialysis (HD) to treat end stage renal disease (ESRD), PD makes use of the internal peritoneal membrane to purify the blood of ESRD patients. The two modalities for carrying out PD are automated peritoneal dialysis (APD) and the manual non-automated procedure of continuous ambulatory peritoneal dialysis (CAPD). According to the latter method, dialysis fluid is exchanged from four to six times throughout the day, every day. The fluid remains inside the patient for about four hours between exchanges and for a much longer period (10–12 hours) at night.

It has become conventional to refer to the basic stages of the PD procedure as FILL, DWELL and DRAIN. In the FILL, stage, dialysate is instilled through a catheter into the peritoneal cavity of a patient.

During the fixed time period known as the DWELL, the dialysate draws soluble waste and excess fluid from blood contained in numerous blood vessels of the peritoneal membrane, by the operation of osmosis and diffusion. Additionally, the dialysate re-balances the electrolyte concentration and corrects for acidosis of the blood.

At the end of the DWELL, spent dialysate is removed from the peritoneal cavity (DRAIN) and discarded. This exchange action must be repeated several times over a twenty-four hour period, as the body continuously produces waste products.

Compared with HD, PD is a very gentle modality, its slow corrective action resembling that of the natural kidney. It is operationally simple, eliminates the need for venipunctures and has low operational costs. Because the system is not an extracorporeal one, there is no need for a high degree of heparinization, a factor which is especially important in the case of diabetic patients.

However, to date HD has continued to dominate in the treatment of ESRD patients. The following aspects of PD may be contributing factors to this state of affairs:

In PD, the peritoneal membrane is exposed to the external environment every time a catheter is connected or disconnected from the solution supply, making infection (peritonitis) a significant problem.

Currently available commercial dialysate for PD exhibits a low pH which is not truly compatible with the biochemistry of the peritoneal membrane. Consequently this bio-incompatibility is believed to be one of the factors which eventually degrades the performance of the membrane with time.

The most popular osmotic agent used in PD dialysates is glucose. Glucose can be absorbed by the body via the peritoneum membrane. This can result in patient obesity and its accompanying complications. Moreover, heat sterilization of the dialysate which contains glucose produces harmful glucose by-products.

Current techniques of PD afford no ability to monitor the pressure build-up in the peritoneum during either DWELL or during the FILL sequence.

Current PD solutions are of fixed composition and cannot be systematically adjusted either in their constituent parts or in the concentration of each constituent during a treatment.

A number of examples of more or less automated peritoneal dialysis machines are to be found in the art, which may be classified into "continuous cycle" PD systems and "batch" PD systems.

In continuous cycle systems, exemplified by U.S. Pat. Nos. 5,004,459 (Peabody et al.) and 5,643,201 (Peabody et al.), the aforementioned DWELL time is essentially zero. Dialysate is delivered by injection into the peritoneal cavity of a patient, simultaneously with the removal of fluid, in a flow-through process.

Continuous cycle processing employs a great amount of dialysis fluid, making it prohibitively expensive for chronic treatment. Known continuous cycle PD systems rely upon the on-site generation of dialysis fluids employing a reverse osmosis water purification unit (connected to an outside water source), and a dialysate proportioning unit, each such unit being about the size of a normal portable household refrigerator. The apparatus is relatively complex, the fluid proportioning itself often comprising more than two independent pumps with fixed proportioning ratios. This leads to difficulties in operation which are complicated by the need for sterilization procedures and pre- and post-sterilization safety tests.

Applications of continuous flow PD systems are limited to treatment of chronic patients, two or three times per week, with the assistance of a competent helper. The intermittent treatment schedule does not provide adequate PD treatment for a number of chronic patients, particularly those exhibiting little or no residual kidney functions. Hence, this type of PD system has fallen almost entirely into disuse.

Known systems for carrying out batch processing, in which there is an appreciable DWELL time during which the effective dialysis step occurs, are exemplified by U.S. Pat. No. 4,096,859 (Agarwal et al.); U.S. Pat. No. 5,141,492 (Dadson et al.); U.S. Pat. No. 5,324,422 (Colleran et al.); and U.S. Pat. No. 5,348,510 (Bryant et al.).

In a continuing effort to provide adequate PD treatment for the varied population of ESRD patients, clinicians have developed a number of different forms of the APD modality of treatment using batch-type PD systems. These include the APD modalities of:

(i) Continuous Cycling Peritoneal Dialysis (CCPD), a method of performing PD in which an automated cycler performs 4 to 6 regular exchanges every night.

(ii) Intermittent Peritoneal Dialysis (IPD), a method of performing PD in hospitals or at home with an automatic cycler two or three times a week for a period of about eight to twenty hours each time.

(iii) Nightly Peritoneal Dialysis (NPD), a method of performing nightly peritoneal dialysis at home for patients with high efficiency peritoneal membranes. Such patients do not fare well with long dialysate DWELL times.

(iv) Tidal Peritoneal Dialysis (TPD). This modality utilizes an initial maximum dialysate fill volume (usually three litres) and periodically, during a long and continuous DWELL time, drains a fraction of the fill volume (usually one third, the tidal volume) and re-infuses about a similar amount, adjusting for ultrafiltration (excess fluid removed from the patient's body during kidney dialysis) into the patient.

However, even the existing batch-type systems have not proven to be entirely satisfactory in addressing real clinical concerns and implementing the above-listed PD modalities effectively. Some of the major limitations presented by existing systems are:

(i) The low pH of the current commercially available dialysate that is not bio-compatible with the peritoneal membrane (reduces the efficiency of the membrane with time).

(ii) Excessive glucose absorption by the patient (glucose is the most popular osmotic agent).

(iii) Harmful by-products of glucose produced during heat sterilization of the dialysate (adverse to the peritoneal membrane and therefore shortens PD lifetime).

(iv) Excessive pressure build-up in the peritoneum during DWELL period (damage to the peritoneal membrane—hernias and leaks).

(v) Inability to monitor the ultrafiltration (UF) rates on-line to determine the effects of medications on the solute transport (vessel dilators or constrictors leading to higher or lower membrane transports respectively), and profoundly affecting adequacy of treatment.

(vi) Lack of any provision for regulating osmotic concentrations or alternating different osmotic agents during treatment (to optimize solute removal).

(vii) Lack of accessories to automatically add accurate dosage of medication on-line to patient during treatment (advantage to children, to diabetics, to geriatrics and, reduction of contamination).

General Description of the Invention

Applicant's overall objective was to provide an automated peritoneal dialysis machine capable of fully "customizing" the composition of dialysate delivered to a patient to meet his or her immediate physiological needs and, to that same end, capable of monitoring the effectiveness of treatment during the treatment process and use this diagnostic information to optimise the customisation process.

It is a particular object of the invention to provide an automated peritoneal dialysis apparatus as aforesaid, including means for metering solutions of osmotic agent, electrolytes and other desired dialysale components from separate solution containers into mixing chamber means for combination, in desired proportions, to provide the desired dialysis fluid and for delivering a selected quantity of said dialysis fluid to the peritoneal cavity of a patient.

It is likewise an object of the present invention to provide automated peritoneal dialysis apparatus as aforesaid, wherein said means for metering dialysate components into the mixing chamber and delivering dialysis fluid to the patient includes means for withdrawing spent dialysis fluid from the patient. According to a preferred embodiment of the invention, a single pump metering means is provided which is capable of performing multiple functions of metering, infusion, proportioning and removal of the dialysis fluid.

It is a still further object of the invention to provide automated peritoneal dialysis apparatus as aforesaid, wherein the means for delivery of fresh dialysis fluid to a patient and for removing spent dialysis fluid from the patient includes means for monitoring interperitoneal pressure and electronic control means responsive to the signal of said pressure monitoring means, for controlling (i) the rates of infusion of fluid into the patient, (ii) the removal of fluid from the patient, and (iii) the customised composition of the dialysate, thereby to allow for control of the patient's intraperitoneal pressure, measurement of peritoneal rates of ultrafiltration and other properties of the peritoneal membrane.

It is a further object of the invention to provide automated peritoneal dialysis as aforesaid, in which the manifold, occlusion means and syringe pump means are housed within a compact integral cartridge. Advantageously, the cartridge is furnished with presterilized container bags of dialysate solution in operative connection to the manifold, as a ready-to-use assembly.

DETAILED DESCRIPTION OF THE INVENTION

Figure 1:
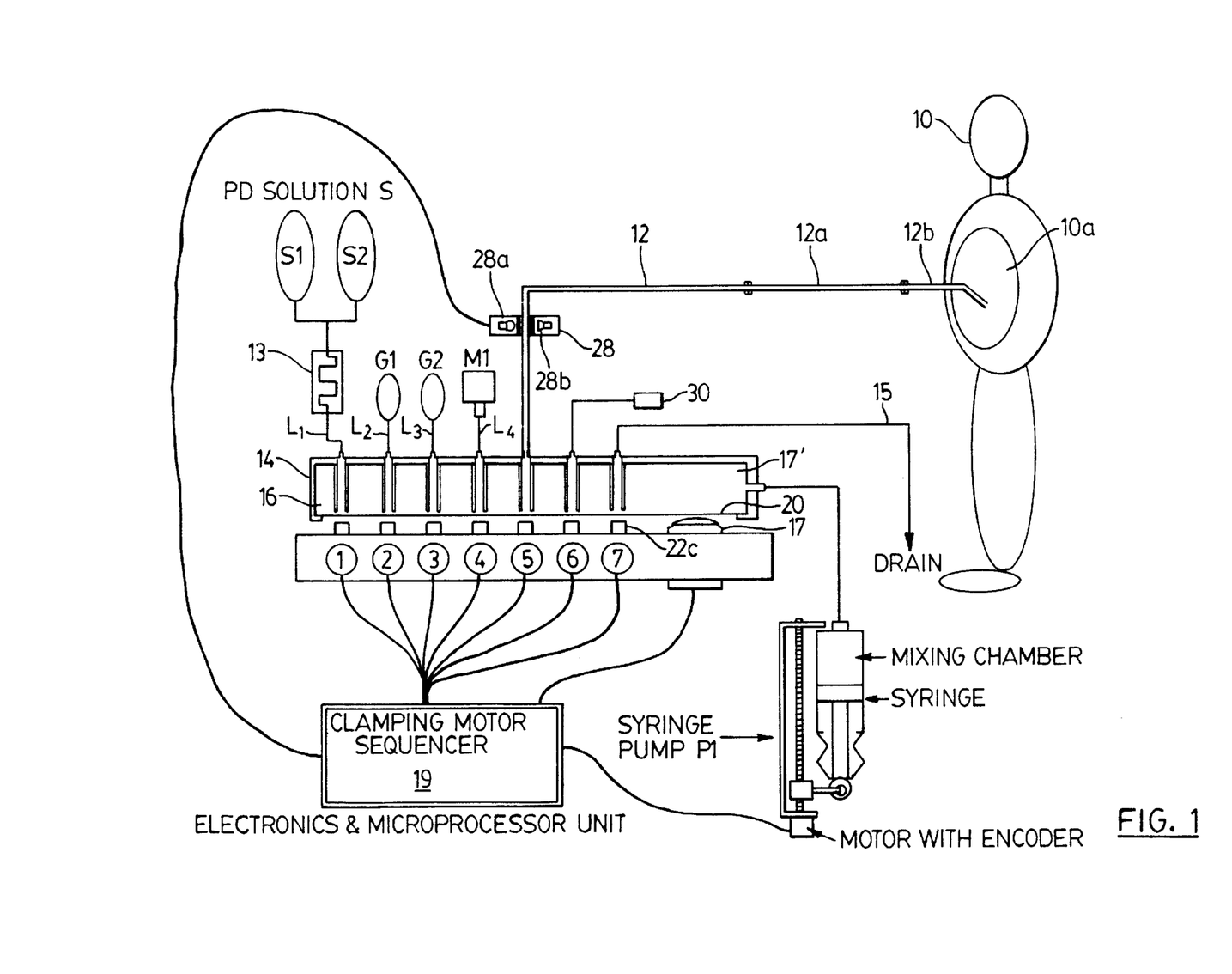
FIG. 1 is a schematic illustration of an embodiment of automated peritoneal dialysis machine according to the present invention.
Figure 2:
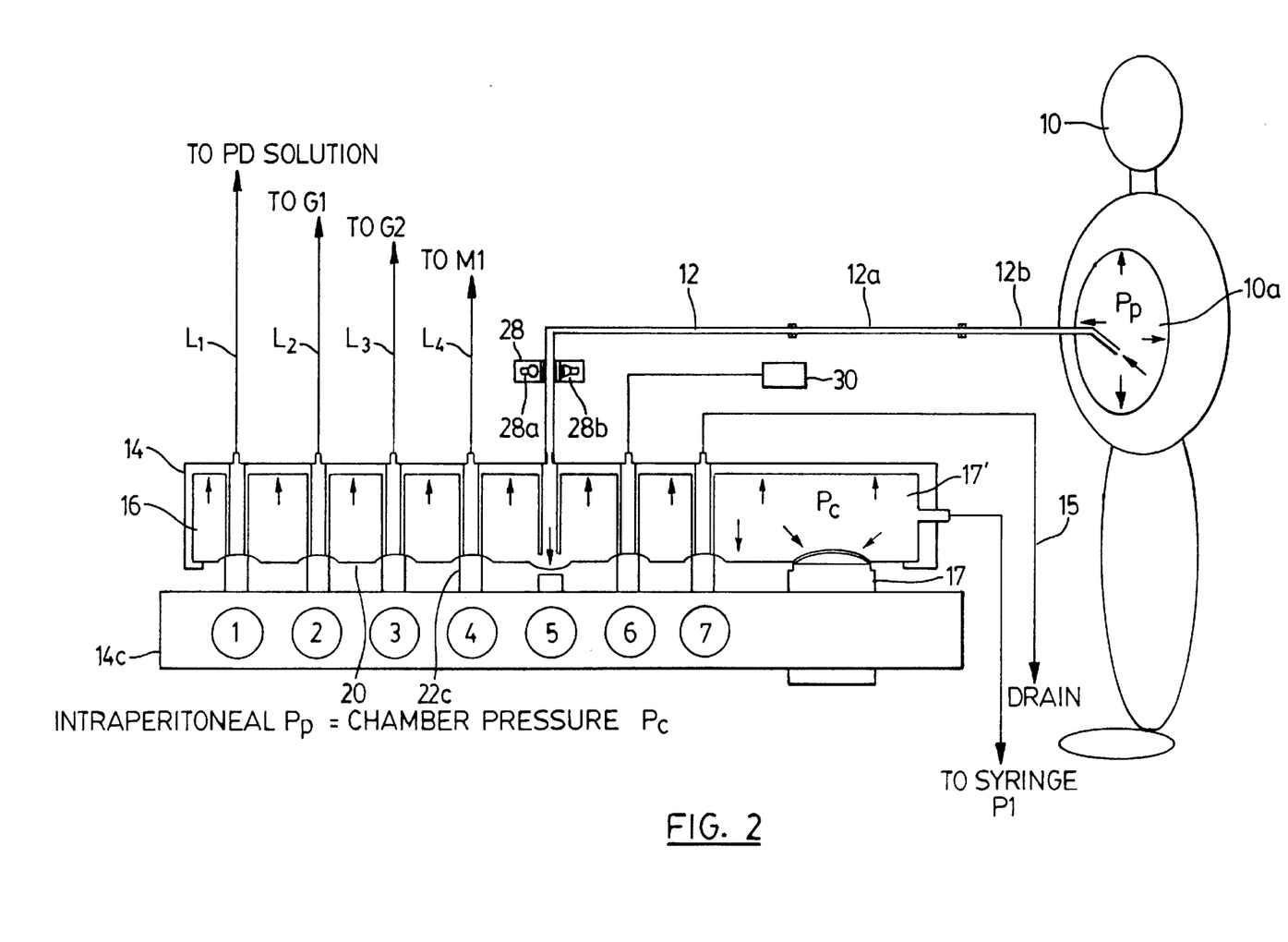
FIG. 2 is a second schematic illustration of the embodiment of FIG. 1, with illustrative emphasis on the use of electronic pressure transducer means for monitoring pressure in the occlusion chamber and hence in the peritoneal cavity of a patient.

A layout of components of apparatus according to the present invention is illustrated schematically in FIGS. 1 and 2. The apparatus is connected to the peritoneal cavity 10a of patient 10 by means of a patient tubing line 12, through which fresh fluid is infused and spent fluid is withdrawn. At its injection end, line 12 is provided with a suitable replaceable extension section 12a and catheter 12b, communicating with the peritoneal cavity 10a.

An essential component of apparatus according to the present invention is an occlusion manifold 14, the hollow interior communication channel (occlusion channel) 16 of which is in communication with all of the fluid input lines to containers of selected dialysate solution components, with output tubing lines to the catheter, a sample collector container and with a drain line.

In the arrangement shown in FIG. 1, seven separate input or output connection ports into channel 16 of cartridge 14 are shown, numbered 1 to 7. Containers (solution bags) S1, S2 carry sterile PD solutions of two different electrolyte compositions and are connected to cartridge input 1 by tubing line L1. In-line heater 13 is provided, as is conventional in PD apparatus, to warm the sterile PD solutions to body temperature. Containers S1 and S2 could alternatively carry standard PD solutions (glucose or similar, as the osmotic agent).

Input 2 of manifold 14 is connected by line L2 to a container G1 of highly concentrated sterile osmotic agent (glucose solution or other known osmotic agent). Container bags G2 and M1 connected by lines L3 and L4, respectively, to the corresponding manifold inputs could contain different medications or additives to improve the clinical value of the solutions in S1 and S2. Apparatus according to the present invention includes precise metering means and means for mixing the metered fluid components together, such as the illustrated syringe pump P1 whose operation is described in more detail below. Aforementioned patient line 12 is connected to input 5, while a drain line 15 is connected to port 7 in the particular arrangement of FIGS. 1 and 2.

For registering and monitoring the interperitoneal pressure during the course of treatment, a pressure transducer means 17 is preferably included, the signal from which is monitored by electronic control means for the apparatus schematically indicated as 19 in FIG. 1.

Figure 3:
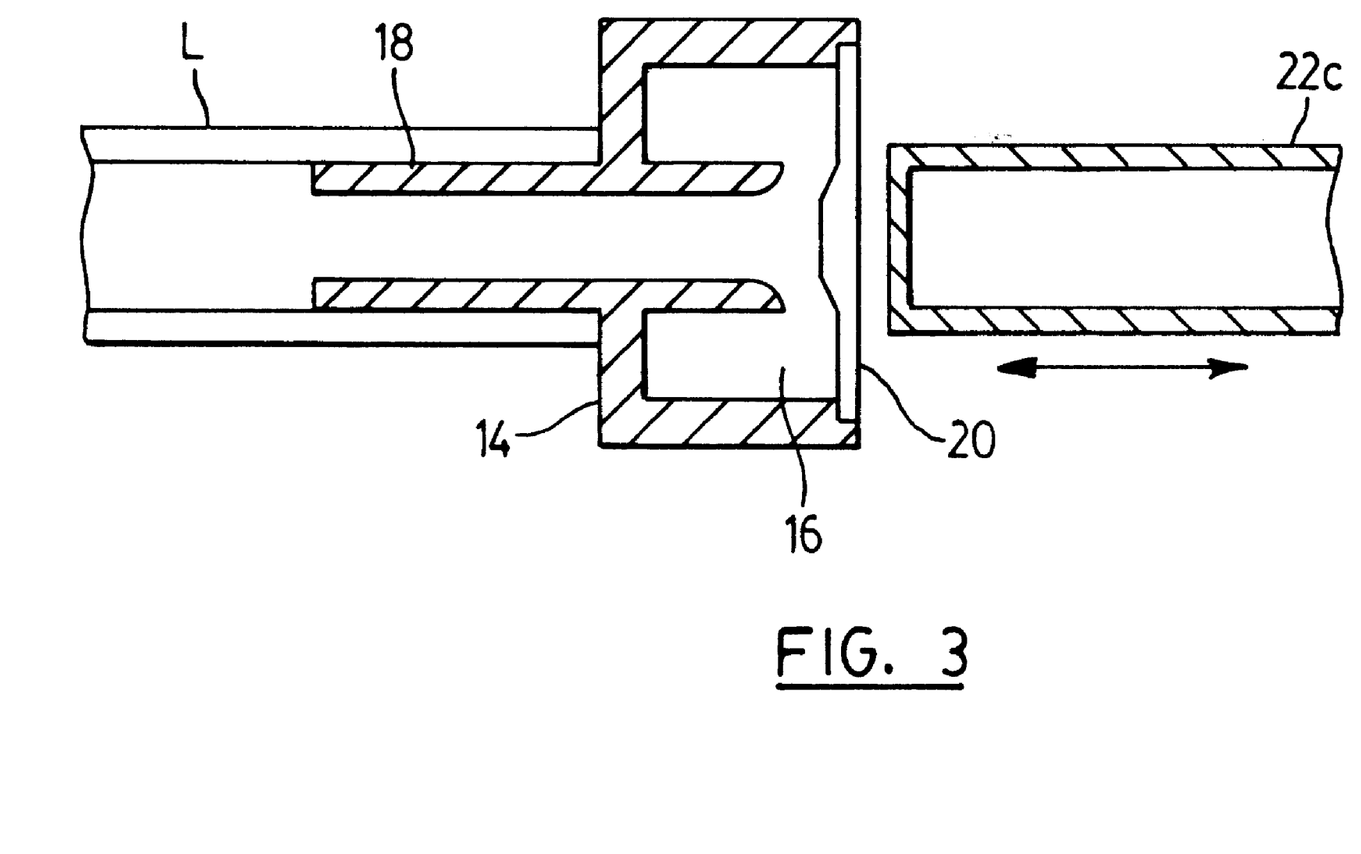
FIG. 3 schematically illustrates one of the liquid input/output ports and a portion of the occluding mechanism in the machine of FIGS. 1 and 2.
Figure 4A:
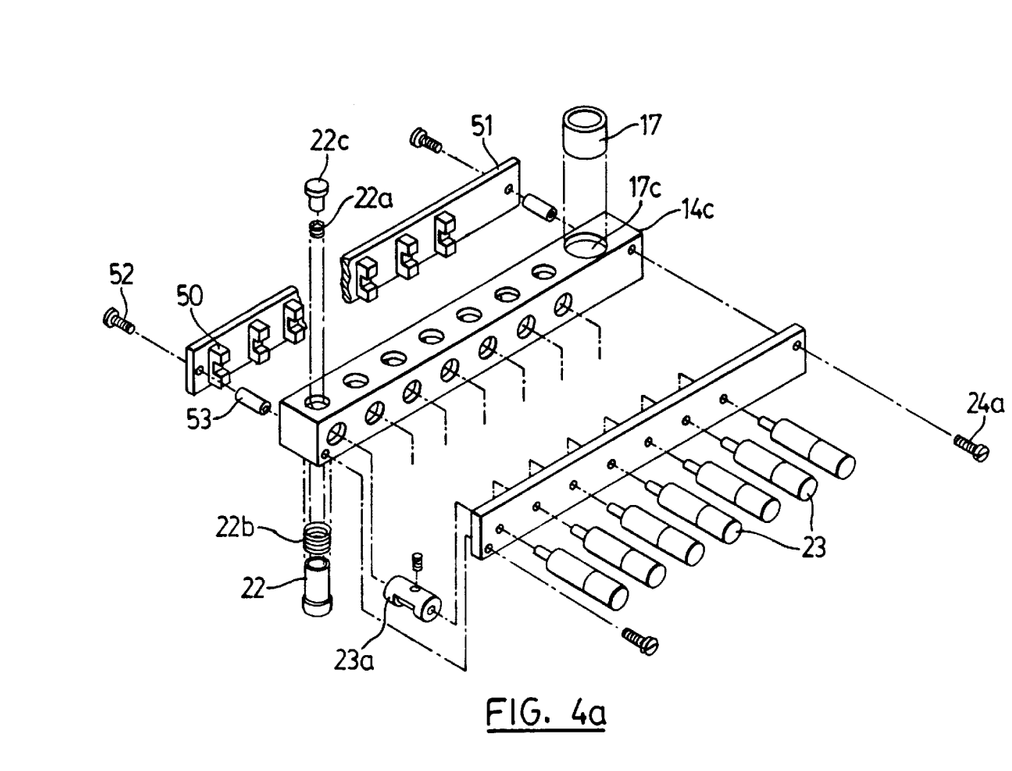
FIGS. 4a and 4b respectively show an exploded view of the occlusion mechanism for an automated peritoneal dialysis machine according to the present invention and a magnified view of the assembly of a single unit thereof.
Figure 4B:
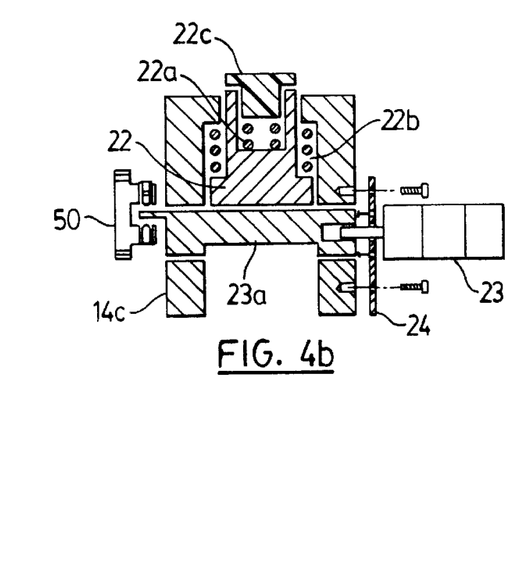

A preferred arrangement for the occlusion mechanism of occlusion manifold 14 is illustrated in FIGS. 3 and 4. FIG. 3 schematically illustrates one of the tubing connecting ports 18 onto which an input tubing line L fits. Port 18 communicates with interior communication channel 16 of occlusion manifold 14.

For each port 18 there is a corresponding flexible sealing diaphragm 20, positioned in the wall of manifold 14 opposite the wall through which corresponding port 18 enters channel 16, and electronically controlled plungers 22.

FIGS. 4a and 4b show exploded views of the assemblies of plungers 22, springs 22a and 22b and motors 23 for an occlusion mechanism of the manifold of automated PD apparatus according to the present invention. In assembly, plungers 22 and plunger springs 22b are first inserted into manifold 14c. Cams 23a attached to individual small rotary motors 23 are inserted into the manifold, so that the plungers are retained inside the manifold by the cams and ride directly on the cams. The small springs 22a and corresponding plunger heads 22c are inserted from the top into respective plungers 22 through the manifold. All the motors 23 are mounted on a motor mounting plate 24. Two screws 24a are used to secure motor mounting plate 24 to manifold 14c.

Each motor 23 rotates its associated cam 23a and corresponding plunger 22c follows the cam for up or down movement. The respective up and down positions of the individual plungers 22 can be sensed electronically by position sensors 50 and a signal sent to the microprocessor means 19 for stopping motors at up or down plunger positions as appropriate. The tubing connecting ports 18 terminating inside channel 16 of manifold 14 align with plungers 22c.

As illustrated in FIG. 2, the "up" position of a plunger has the effect of occluding the cartridge port to which it corresponds, while the "down" position opens the port. Fluid flows may accordingly be controlled as discussed below.

It is contemplated that the machine will be controlled by microprocessor means 19, having stored memory for on-line monitoring of information and for programming of set operational parameters. A removable memory card can also be incorporated to ensure easy collection and transfer of treatment data for the patients. optionally, an interactive voice interface and visual and audio alarm systems can be incorporated to simplify the diagnosis of problems during and after PD treatments.

The microprocessor means 19 is programmed for receiving signals from various sensors and for producing output control signals for controlling the metering pump P1 and plungers 22 through electromechanical means such as the motor/cam arrangement discussed above.

During dialysis, the desired filling fluid volumes of each cycle and the FILL, DWELL and DRAIN duration times are programmed into the microprocessor. The ratios of the corresponding medications, osmotic agents and/or additives are also entered. Initializing the machine operation, all input and output ports of the cartridge 14 are closed by their respective plungers 22. These plungers are controlled individually by their respective motors. When plunger head 22c moves upwards (i.e., toward the manifold), it pushes against flexible diaphragm 20, closing the outlet of port tube 18 within channel 16 of the manifold, precluding entry or withdrawal of fluid from the chamber by way of that port. Moving the plunger downward leaves the tube outlet in communication with the chamber, so that fluid may flow freely in or out of the chamber and communicate with any other outlets which are also open at that time.

Referring to FIGS. 1 and 2, to "flush" the tubing set, the microprocessor electronic control means is programmed so that port #1 (to solution S1 and S2) is opened. The metering pump P1 operates to draw in fluid from S1 and S2. Port #1 is then closed and port #7 (Drain Line) is opened. The metering pump P1 operates once again to expel the drawn in fluid out through the Drain Line. In sequence, the plungers corresponding to input/output ports numbers 2, 3 and 4 are activated thus opening and closing input ports 2, 3 and 4 at predetermined times. During the opening period of each port, the metering pump Pi operates to draw fluid in from respective container bags and to flush the fluids out to the drain. Patient line 12 is flushed by opening #1, drawing fluid from S1 and S2, then closing port #1 and opening port #7 and infusing the fluid into patient line 12.

For efficient operation in drawing calibrated volumes of fluid from container bags and infusing the withdrawn fluid to target locations, whether the container bags and the target locations are vertically above or below the machine, it is essential that metering pump P1 provide positive displacement of fluid and have a known volumetric displacement. One way this has been arranged in practice has been to have a variable volumetric displacement mechanism included in the metering pump P1. Variable displacement was achieved with controlled linear translation of a volume displacement member. This type of motion was achieved by coupling a worm gear to the output driveshaft of an electric motor. The controlled rotary motion of the electric motor is then smoothly translated into a controlled linear motion which in turn will adjust the volumetric displacement of the pump.

A common example of this type of metering pump is a syringe pump with controlled linear translation of the plunger in the barrel of the syringe. The linear motion (volume displacement) of a metering syringe pump was calibrated in the following manner. The internal shaft on the electric motor was digitally encoded. Its rotary position was optically sensed thus generating a set of electrical pulses whose number were directly proportional to linear displacement of the worm gear. One particular configuration which was used in this way gave a fluid displacement of 20 cc for each 2.15 inches of linear travel of the worm gear. The lead screw of the worm gear had a lead of 0.12 inches and was driven through a gear box (gear ratio 81:1). The encoder of the motor produced 512 pulses/revolution. The microprocessor control means, through linkage to the motor shaft encoder, could track each pulse generated by the encoder. In principle this metering system had a sensitivity of 30×10$^{-9}$ litres. This is at least 3 orders of magnitude more precise than required for APD apparatus according to the invention to achieve its metering objectives. Naturally those skilled in the art could construct a number of variations of this particular device.

During FILL mode (filling the patient), port #1 would be opened and the metering pump activated to draw the correct amount of fluid from container bags S1 and S2. That done, port #1 closes and desired additives G1 selected by opening port #2, drawing the correct volume into P1, then closing port #2. Continuing in this way, incremental additions to the fluid in the syringe pump can be made in the desired ratios with fluids from G2 and Ml by opening and closing ports #3 and #4 accordingly. The drawn fluids mix thoroughly inside the syringe body (the Mixing Chamber). Then, to infuse the proportioned metered fluid composition into the patient, port #5 opens and the metering pump causes the fluid inside the syringe body to be injected into the peritoneal cavity of the patient, while the machine monitors the pressure and the volume of fluid instilled into the patient.

Figure 5:
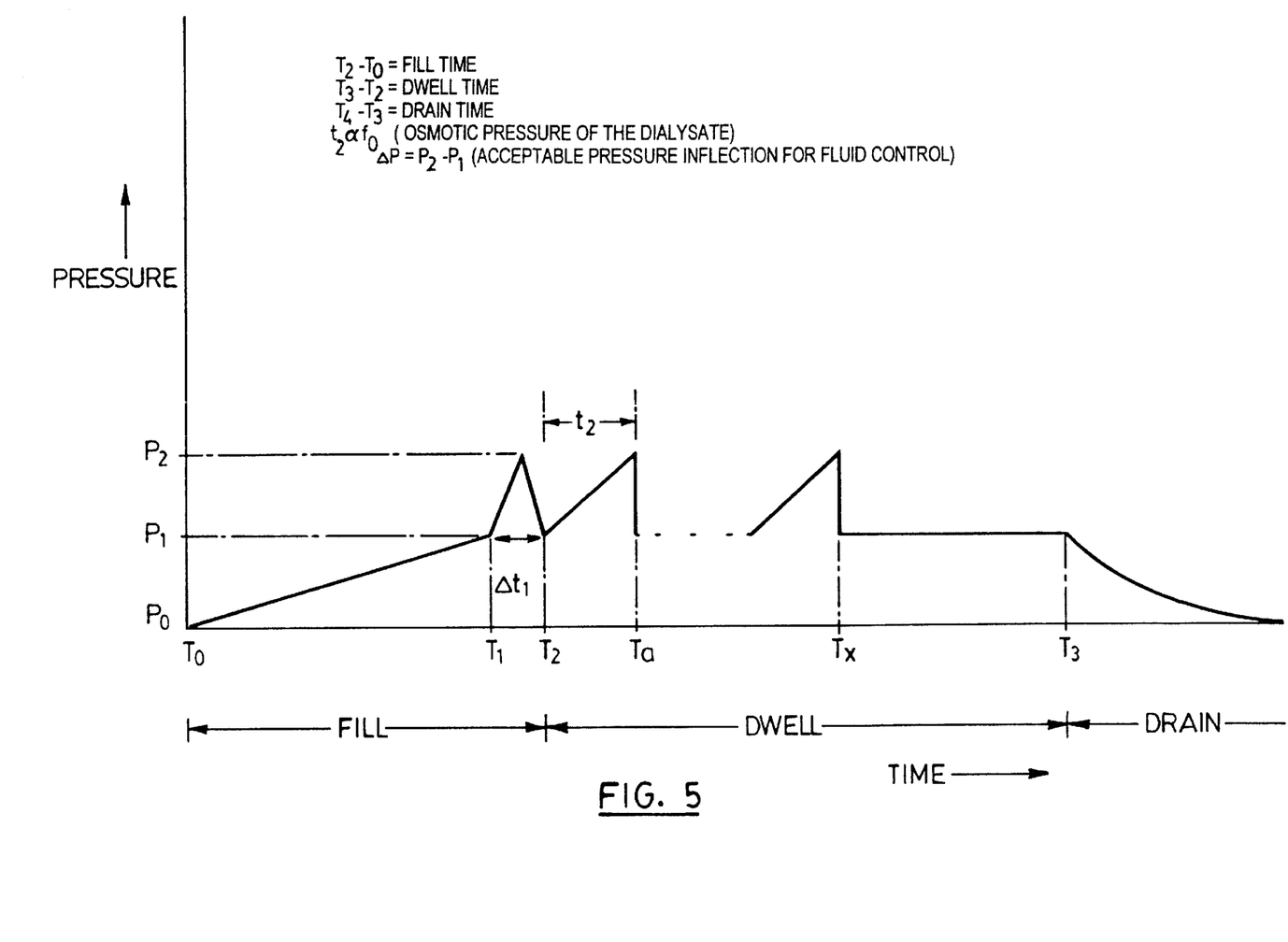
FIG. 5 is a graphical representation of the variation of intraperitoneal pressure versus time, during the cycles of an apparatus according to the present invention.

This injection procedure is repeated several times until the correct total amount of dialysis fluid has been delivered or some other predetermined state is achieved. A graphical example of such a predetermined state is shown in FIG. 5 at point P2. During the FILL mode, the intraperitoneal pressure will increase slowly from $P_0$ at time $T_0$ to $P_1$ at time $T_1$ and in proportion to the filled volume. There is an inflective increase in pressure at the maximum fill volume attained at time beyond $T_1$ and corresponding pressure $P_2$. The machine will be programmed to remove enough fluid to back off the pressure from the maximum $P_2$ to a safe and controlled pressure level $P_1$. This would be the steady state pressure for the monitoring process during the DWELL time. The official DWELL period then begins at $T_2$.

As discussed later below, the gradient (dp/dT) of the inflective pressure at the time $T_1$ during the FILL state, could be used therapeutically to correlate to the elastic properties of the peritoneal membrane. It is therefore possible to track and/or predict the ageing of the peritoneal membrane.

Turning to the DWELL period, all ports of the manifold are closed except port #5, which is opened to enable fluid communication between the peritoneal cavity and the occlusion chamber through the catheter, the transfer set and the patient line. The pressure in the peritoneal cavity is transmitted equally through the peritoneal dialysis fluid (a continuous fluid path), to all the above fluid containing parts. As illustrated in FIG. 2, the pressure in the occlusion chamber is directly transmitted through the flexible diaphragm to the pressure transducer 17 which is in direct contact with diaphragm 20. The pressure transducer sends proportional electrical signals to the electronic and microprocessor unit (the Control Unit), for processing, for controlling and for visual displays accordingly. The information so developed is also useful for other purposes as explained elsewhere herein.

At relatively static state (no fluid flow), the interperitoneal pressure Pp is equal to the chamber pressure Pc. Thus variations in the interperitoneal pressure are monitored by the microprocessor from signals transmitted by in-line pressure transducer 17. Any ultrafiltration which occurs (drawing fluid from the body of the patient into the peritoneal cavity) will necessarily result in an increase in intraperitoneal pressure which, on detection by the pressure transducer 17, signals the control means to activate Pump P1 to suck back sufficient fluid, namely, the excess amount, from the patient's peritoneal cavity until the steady state pressure level ($P_1$) has been restored. The volume which has been so removed during the DWELL period is recorded by the computer as "ultrafiltration" (UF), with respect to the time it was taken. Whenever the pressure reaches $P_2$, the pump is activated to reduce the fluid volume enough to drop the pressure back to the steady state $P_1$. This volume $V_f$ is recorded with respect to time $t_2$ (the length of this time will be dependent on osmotic pressure of the fluid and the diffusion efficiency of the peritoneal membrane).

Knowing the osmotic concentration of the dialysis fluid, the diffusion efficiency of the peritoneal membrane can be quantified for the first time in vivo. This action is operated as often as it may be necessary and the cumulated UF is displayed with respect to real time.

Figure 6:
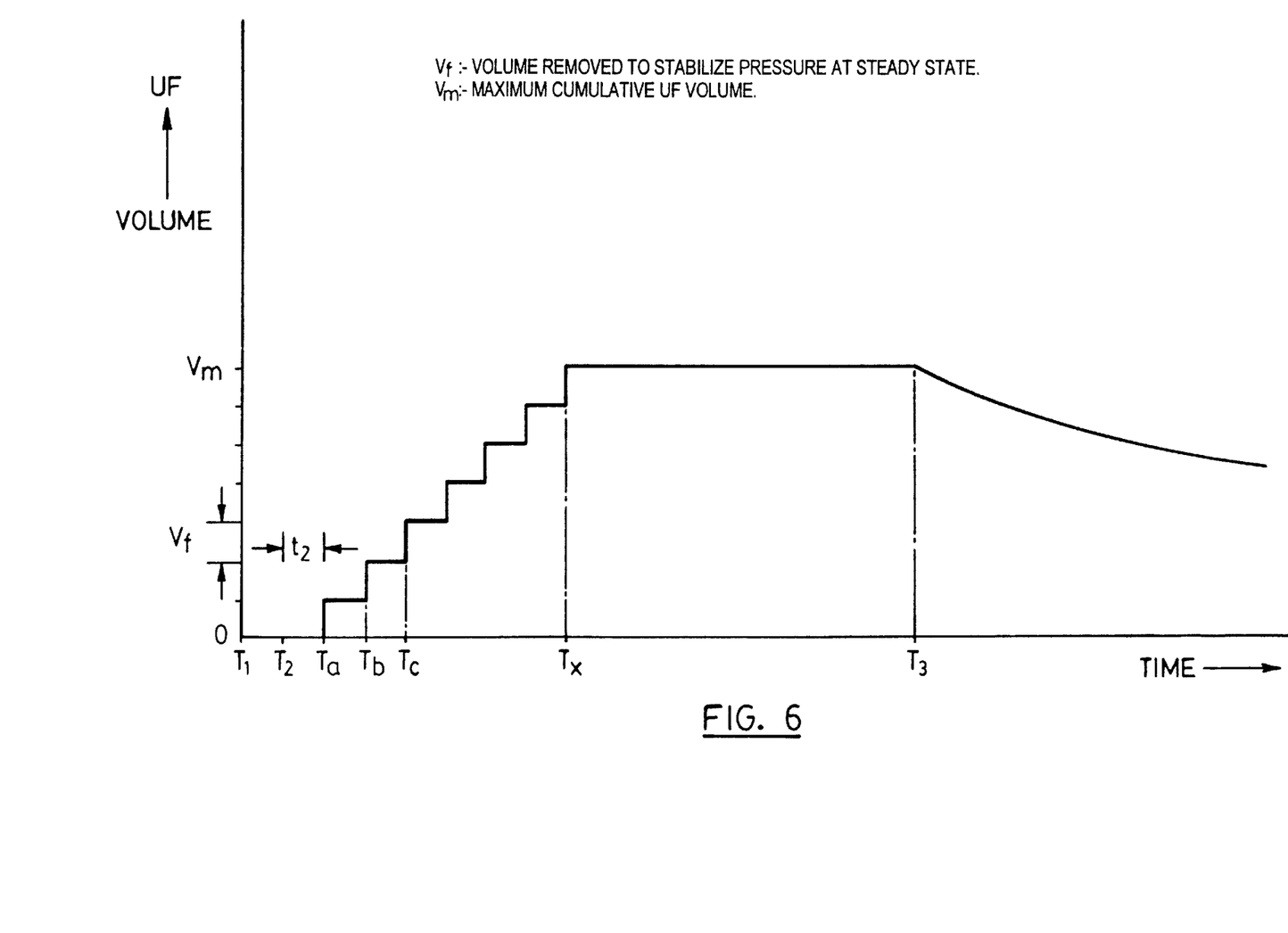
FIG. 6 is a graphical representation of the volume of fluid removed (ultrafiltration UP) to stabilize pressure as a function of time during the DWELL of a dialysis cycle, as measured using a PD apparatus according to the present invention.

This process of restoring steady state pressure and recording the cumulative volume of fluid removed as a function of time is carried out automatically throughout the DWELL period and the measure of cumulative ultrafiltration (UF) is recorded, as illustrated in FIG. 6. A graphical measurement of intraperitoneal pressure versus time affords further valuable diagnostic information not available in the current state of the PD art. When the pressure does not change from its steady state value for a predetermined period of time, it may be inferred that the dialysis fluid is no longer performing its optimal clinical function. At such a time, $T_3$ (FIG. 5), the fluid can be safely drained out of the patient without waste of further time. Onset of a steady pressure drop, however, would indicate that the patient is absorbing fluid from the peritoneal cavity which could indicate that the patient is absorbing glucose from the dialysate. A rapid drop in pressure would signal that dialysate is leaking into extra-abdominal tissues. These undesirable clinical conditions are avoided by arranging the control logic of the machine to automatically drain out all spent dialysate volume from the patient when such pressure drop occurs. It is in the DWELL stage that the most significant dialytic treatment occurs.

During the DRAIN mode port #5 is opened. The metering pump P1 draws the spent fluid from the patient and into the body of syringe P1. This volume is measured as it is being withdrawn. When the syringe is full, port #5 closes and port #7 opens. The pump P1 reverses its direction and pushes the waste fluid from the syringe through the drain line and into a receptacle for spent dialysate. Then port #7 is closed, port #5 is re-opened, and the procedure repeated. This is operated until all the fluid is drained from the patient or until the pressure registers negative, or until the end of the set DRAIN time. The final UF is then determined by the machine.

This completes one dialysis cycle. The above procedure is repeated as many times as required until the desired amount of treatment is obtained.

Another important characteristic of this invention is its ability to make decisions based on real-time physiological needs of a patient or provide previously unattainable clinical information.

A graphical representation of the on-line monitoring of volume of fluid removed in order to stabilize pressure at a steady state, as a function of time during the DWELL period of one dialysis cycle, is provided in FIG. 6 and is but one such example of new clinical information. The invention will allow the normal set DWELL time ($T_2$ to $T_3$) to be rationally adjusted. At maximum UF volume, $V_m$, the dialysis fluid has reached equilibrium with the plasma in the peritoneal membrane. Therefore for any time beyond $T_x$, treatment time is potentially wasted. As mentioned above, a clinician could either program the machine to automatically drain the patient of the spent fluid and introduce fresh fluid for better dialysis or use the information to set more effective DWELL time for the next treatment.

Alternatively if the set DWELL time terminates at the rising phase of the ultrafiltration curve, (i.e., at a time which is less than $T_x$) then the dialysate is not being utilized properly.

These are some examples of the ability of the apparatus to automatically make decisions based on realtime physiological needs of a patient. Other examples would be obvious to those skilled in the art of peritoneal dialysis. The graph of FIG. 6 also reflects real time solute and fluid transport rates of the peritoneal membrane for any given dialysate formulation. That is, the greater the efficiency of the peritoneal membrane the greater the initial slope of the ultrafiltration curve and or the faster time $T_x$ is achieved.

Significantly, the effect of various drugs on the peritoneal membrane will be directly reflected in the changes of the membrane transport characteristics. For the first time clinicians will be able to quantify the transport characteristics of the peritoneal membrane and the effects of drugs on dialysis patients on-line and use this information to directly control the machine and/or medications or allow the machine to make the necessary adjustments automatically. This suggests the possibility of using the method of the present invention in pharmacokinetics studies of the effect of therapeutic agents on the peritoneal dialysis treatment of patients with renal disease.

A further example of the capability of apparatus according to the invention in providing previously unattainable clinical information and/or intelligent use of such information by the APD machine is as follows: In clinical PD applications, the characteristics of the peritoneal membrane with respect to its active surface area, and permeability (solute and fluid transport) are all variable and mostly unknown for any given patient. Hence methods have been developed to quantify peritoneal membrane performance. However, these methods are complex, indirect and none of them are on-line analytical procedures. Two methods used for assessing membrane performance are (a) the peritoneal Membrane Mass Transfer Area Coefficient (MTAC) and (b) the Peritoneal Equilibration Test (PET). The later (PET), determines the ratio of dialysate-to-plasma (D/P) of a given solute and is the one most commonly used to assess patients. At best this is performed once a month. Currently it is impossible to obtain data to perform PET at various stages of the DWELL period during treatment. If this time dependent data could be obtained it could lead to a better clinical understanding of the different types of ultrafiltration failures. Combining the unique ability of apparatus according to the present invention to secure a sample of the fluid during DWELL at known correlated points on the ultrafiltration curve clinicians will be better able to properly evaluate the PD treatment in vivo, and to track the ageing of the peritoneal membrane or degradation of its performance.

During the FILL period (FIG. 5), the increasing interperitoneal pressure is continuously tracked. At the maximum fill volume (corresponding to pressure P1), the additional instilled fluid would produce a sharp rise in pressure to P2 (the cavity is full—additional fluid therefore over stretches the membrane). The slope of this sudden pressure rise will be proportional to the elasticity of the peritoneal membrane, that is $$(P1-P2)/dt = dP/dt \, E$$

where E is the membrane elasticity, dP is differential pressure and dt is the differential time. As the peritoneum ages or deteriorates, the elasticity of the membrane weakens and E decreases. Hence the values of the recorded dP/dt could be used, for the first time, to assess the ageing or the effects of drugs on the membrane. Using the ultrafiltration parameters, it is also possible to monitor and quantify accordingly the effects on the peritoneal membrane caused by drugs or by concurrent illness.

These represent major advances in the art of PD treatment. An in vivo related clinical advantage is that clinicians will immediately be able to correlate changes in ultrafiltration curve with the type of medication or additive used during a treatment cycle.

It will be appreciated from the foregoing that the pressure monitoring activities used to control the UF using a machine according to the present invention makes it possible to perform a true tidal peritoneal dialysis. By maintaining the pressure at its initial fill pressure $P_1$ we can infer that the actual volume of fluid in the cavity is the same at all times during DWELL as the initial fill volume. This volume is known. For the first time an APD machine will be able to use the actual volume of fluid in the peritoneal cavity and not a pre-estimated amount to determine the actual tidal withdrawal and refill volumes. This is a major improvement in the art.

Moreover, additional detectors and sensors may be included in the system and their signals taken into account to a programme microprocessor or diagnostic and therapeutic advantage. For example, a turbidimeter including a light source and light detector monitoring the clarity of the effluent during DRAIN can give early detection of the onset of infection. If patient line 12 is passed between such a light source and light detector, it will be possible to detect whether or not the patient's effluent is cloudy during DRAIN, owing to an onset of peritonitis (production of enhanced level of light-scattering white blood cells brought about by infection). The detector will transmit this information to the microprocessor and audio and visual alarms may be initiated, the machine triggered to empty metering pump P1 and a sample of cloudy effluent collected for further analysis. The machine could be programmed to initiate a protocol for peritonitis treatment (i.e., to initiate "lavage" and administer antibodies).

The machine could therefore be programmed to make important decisions as to the infusion pattern on the basis of signals from sensors reflecting the composition and pressure of fluid in the peritoneal cavity.

Alternative Embodiments of Apparatus

Although the apparatus embodiments shown in FIG. 1 employs a syringe pump to draw and deliver the apportioned dialysate components, the arrangement could be used without a metering pump at all, but employing a weighing system and gravity for the discharge of sterile fluids and medications from container bags supported vertically above the patient, with a weigh bag located below the patient for determining the drained volume.

Equally as valid, although the basic machine is designed to customize the dialysate from a plurality of solution bags, the machine can be used in a non customisation mode, i.e., with dialysate pre-mixed in each of one or more container bags. Each port can be connected to a dialysate of fixed formulation. The described diagnostic power of the apparatus can then be used to select which port is connected to the patient line (12) to FILL the patient, determine the DWELL period, and drain the patient of that selected formulation using the metering pump.

Figure 7:
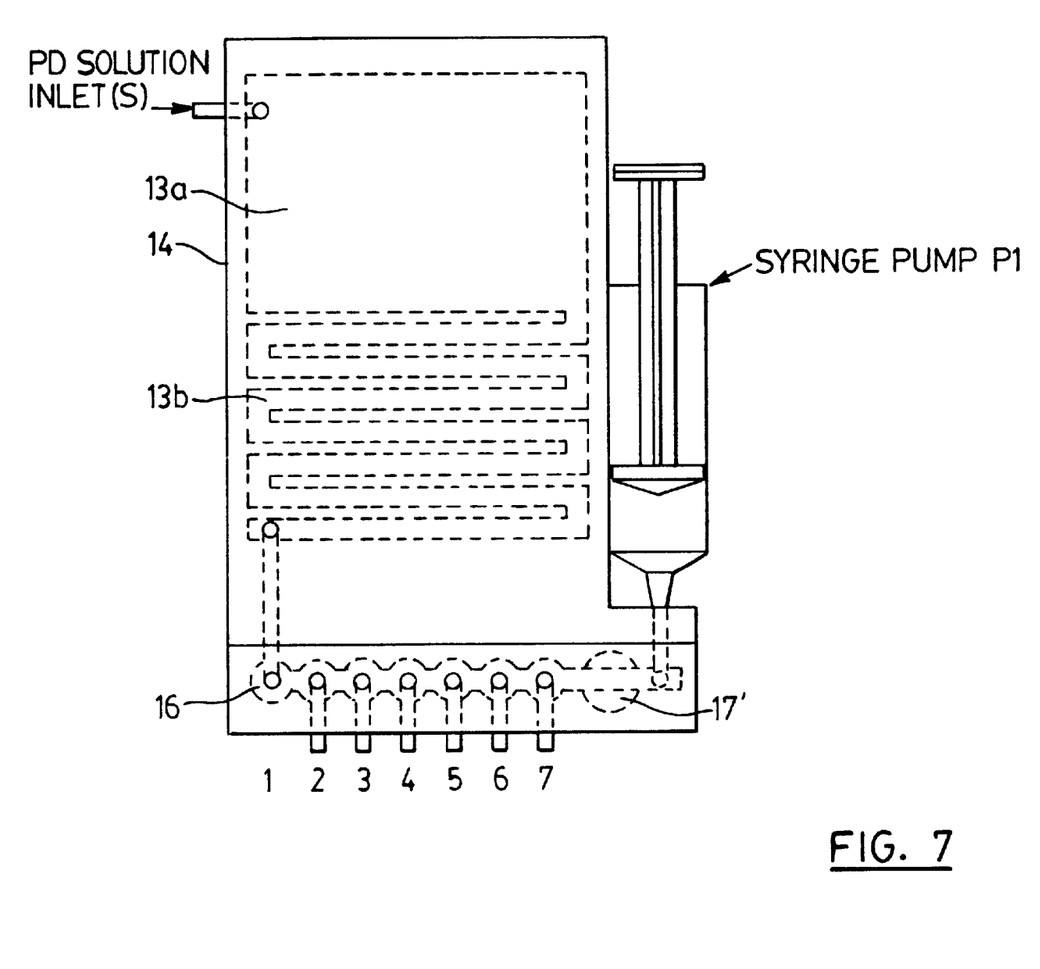
FIG. 7 is a preferred version of the apparatus according to the invention, in which the working components are structurally integrated into a compact cartridge.

A "compact cartridge" version of the system of FIGS. 1 and 2 is as shown in FIG. 7. The occlusion block 14, the heater and metering pump P1 are all integrated into a single compact cartridge. The heating chamber is divided into two sections: initial heater chamber 13a that houses the incoming cold solution, and a corrugated heater section 13b that directs the fluid path to ensure proper heating of the solution. The output of the heater is attached to port #1.

It is also contemplated that to further reduce infection rate often caused by poor clinical practices of the patients, the complete cartridge and the solution bags could be manufactured, assembled together and supplied pre-sterilized and ready for use.

The operation of this embodiment also has (a) an effluent detector 28 located on Patient Line and (b) a sample collector port (at #6). The drain line 15 is in this arrangement located at port #7.

The effluent detector 28 comprises a light source 28a facing a light detector 28b. Variations in the light intensities are detected by the light detector and the signals transmitted to microprocessor for the appropriate actions.

The patient line 12 passes between the light source 28a and the light detector 28b of the effluent detector 28. Hence during DRAIN if the patient's effluent is cloudy (due to an onset of peritonitis; infection-production of white blood cells), the light beam to the light detector is diffused. The detector transmits the message accordingly to the microprocessor. Both audio and visual alarms are initiated. When this happens the machine automatically, at the point of emptying the metering pump P1, opens port #6 and sends a sample of the cloudy effluent solution into the sample collector container 30 (which could be a bag or a syringe). Then port #6 will be closed and the normal drain procedure will be continued by operating port ∩7.

If the apparatus had been set up to initiate peritonitis treatment, rapid peritoneum flush or flushes (fills immediately followed by drains), will be carried out. Then followed by treatment fill volumes containing medication or medications, automatically metered from the medication containers such as $M_1$, by the metering pump P1.

The effluent detector, similarly, will detect excessive amount of blood in the effluent (usually with new catheter operations or with breaking in an new catheter), and could be programmed to automatically reduce the amount of heparin additive, or to reduce the dialysate infusion volumes (particularly where there is "leakage" from the point of entry of the catheter).

While particular embodiments of this invention have been described in relation to the accompanying drawings, it will be evident to those skilled in the art that changes and modifications may be made therein, without departure from the spirit of the invention as defined in the appended claims.

I claim:

1. Apparatus for carrying out peritoneal dialysis on a patient whose peritoneal cavity is in communication with at least one patient catheter, said apparatus comprising:
   (a) a manifold comprising a plurality of liquid input/output ports;
   (b) occlusion means for selectively sealing off and re-opening communication between any one or more of said input/output ports and the other input/output ports of the manifold;
   (c) a patient conduit line for connecting at least a second one of said input/output ports to said patient catheter;
   (d) conduit lines for connecting others of said input/output ports to respective container bags of dialysate solution components; and
   (e) metering means in communication with at least a first one of said input/output ports, operable to withdraw and measure volume of a selected quantity of liquid from said manifold and to allow the mixing together of selected quantities of components of said dialysate solution to provide a dialysis solution of a desired final formulation; and
   (f) electronic control and sequencing means for controlling said occlusion means and said metering means, operable to cause the selected volume of each of selected ones of said components to be withdrawn by said metering means and further operable to cause a selected volume of said dialysis solution of a desired final formulation to be injected through said patient conduit line into a peritoneal cavity line of the patient in a FILL phase and, after a first selected time in a DWELL phase, to be withdrawn from the peritoneal cavity into said metering means.

2. Apparatus according to claim 1, further comprising a drain conduit line for connecting a third one of said input/output ports to a receptacle for spent dialysate, said electronic control and sequencing means being operable in a DRIN phase following said first selected time to cause all or part of the spent dialysis solution withdrawn into said metering means to be injected through said drain conduit line into said receptacle.

3. Apparatus according to claim 1, wherein said metering means comprises fluid transfer means including a pumping mechanism and reservoir means of calibrated variable volume, and electromechanical drive means operable to vary the volume of said reservoir means in a program of stepped increases or decreases of said calibrated volume in response to control signals from said electronic control and sequencing means.

4. Apparatus according to claim 3, wherein said metering means comprises a syringe pump having a syringe plunger and electromechanical drive means for stepped advancement or retraction of said syringe plunger in response to control signals from said electronic control and sequencing means, for producing selected fixed or variable fluid proportioning ratios.

5. Apparatus according to claim 4, wherein said manifold, said occlusion means and said syringe pump are housed within an integral cartridge assembly.

6. Apparatus according to claim 5, further including pre-sterilized container bags of dialysate solution in operative connection to said manifold.

7. Apparatus according to claim 2, further comprising means for monitoring the intraperitoneal pressure of the patient and producing a first monitoring signal to said electronic control and sequencing means for use in determining and implementing operation steps of the apparatus appropriate to desired therapeutic treatment of the patient.

8. Apparatus according to claim 7, wherein said operation steps of the apparatus are for the determination or control of ultrafiltration during dialysis treatment of a patient.

9. Apparatus according to claim 7, wherein said operation steps are appropriate to determine elasticity or ageing of the peritoneal membrane of a patient undergoing peritoneal dialysis.

10. Apparatus according to claim 2, further comprising electro-optical means for producing a second monitoring signal to said electronic control and sequencing means, said second monitoring signal being indicative of turbidity of fluid in said patient conduit line at a selected time, for use in determining and implementing operations of the apparatus appropriate to desired therapeutic treatment of the patient.

11. A method for carrying out peritoneal dialysis on a patient whose peritoneal cavity is in communication with at least one patient catheter, said method comprising the step of maintaining liquid pressure in the peritoneal cavity at a selected value during a DWELL phase, by removing excess liquid from, or injection additional dialysate solution into the peritoneal cavity, in response to changes in the peritoneal cavity liquid pressure, and determining ultrafiltration during said DWELL phase from measurements of the excess liquid removed or the additional dialysate solution injected.

12. A method for carrying out peritoneal dialysis on a patient whose peritoneal cavity communicates with at least one patient catheter, the method comprising the steps of:

(a) providing an apparatus which includes
 a manifold with a plurality of liquid input/output ports,
 occlusion means for selectively sealing off and re-opening communication between any one or more of said input/output ports and the other input/output ports of said manifold,
 metering means in communication with at least a first one of said input/output ports, operable to withdraw and measure a volume of selected quantities of liquid from said manifold and to inject selected volumes of liquid into said manifold,
 means for injecting selected volumes of liquid from said manifold into a mixing chamber;
 a patient conduit line for connecting at least a second one of said input/output ports to said patient catheter, and
 conduit lines for connecting others of said input/output ports to respective container bags of dialysate solution components;

(b) using electronic control and sequencing means, operable to control operation of said occlusion means and metering means, in conjunction with sensor means operable to convey monitoring signals to said electronic control and sequencing means indicative of a condition of liquid in the peritoneal cavity of the patient, in an automatic mode in which said control and sequencing means causes (i) a selected volume of each of selected ones of said dialysate solution components to be withdrawn by said metering means to provide a dialysis solution in said mixing chamber of any desired final composition or formulation, (ii) a selected volume of said dialysis solution to be subsequently injected through said patient conduit into the peritoneal cavity in a FILL phase and, (iii) after a selected dwell time during a DWELL phase at least a portion of spent dialysis solution to be withdrawn from the peritoneal cavity into said metering means.

13. A method according to claim 12, wherein said selected dwell time is determined by monitoring signals received by said electronic control and sequencing means.

14. A method according to claim 12, wherein said apparatus provided to carry out the method further includes a drain conduit line for connecting a third one of said input/output ports to a receptacle for spent dialysate, and wherein said electronic control and sequencing means is used in a DRAIN phase following said selected dwell time to cause the apparatus to withdraw all or part of the spent dialysis solution into said metering means and to be injected through said drain conduit line into said receptacle.

15. A method according to claim 14, wherein said sensor means comprises pressure transducer means operable to produce a monitoring signal indicative of intraperitoneal pressure in the patient.

16. A method according to claim 14, wherein said sensor means comprises electro-optical means for producing a monitor signal indicative of turbidity of fluid in said patient conduit line.

17. A method according to claim 15, wherein said automatic mode of operation includes maintaining liquid pressure in the peritoneal cavity at a selected value by causing the apparatus to remove excess solution from, or inject additional dialysate solution into the peritoneal cavity, in response to the monitoring signals from said pressure transducer means.

18. A method according to claim 17, further comprising the step of measuring as a function of time volume of excess solution removed from the peritoneal cavity of the patient to maintain substantially constant intraperitoneal pressure to characterize transport characteristics of a peritoneal membrane of a patient being treated.

19. The method of claim 11, wherein during said DWELL phase, a selected quantity of dialysis fluid is withdrawn from the peritoneal cavity and returned to the peritoneal cavity a selected number of times in order to agitate and homogenize the fluid.

* * * * *